US008828689B2

(12) United States Patent
Caimi et al.

(10) Patent No.: US 8,828,689 B2
(45) Date of Patent: *Sep. 9, 2014

(54) INCREASED POLY (α 1, 3 GLUCAN) YIELD USING BORIC ACID

(71) Applicant: E I du Pont de Nemours and Company, Wilmington, DE (US)

(72) Inventors: Perry G Caimi, Kennett Square, PA (US); Susan Marie Hennessey, Avondale, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/719,261

(22) Filed: Dec. 19, 2012

(65) Prior Publication Data

US 2013/0157316 A1    Jun. 20, 2013

Related U.S. Application Data

(60) Provisional application No. 61/577,274, filed on Dec. 19, 2011.

(51) Int. Cl.
  *C12P 19/18*    (2006.01)
  *C12N 9/10*    (2006.01)

(52) U.S. Cl.
  CPC .................................... *C12P 19/18* (2013.01)
  USPC ............................................ 435/97; 435/193

(58) Field of Classification Search
  None
  See application file for complete search history.

(56) References Cited

U.S. PATENT DOCUMENTS 3,689,362 A * 9/1972 Takasaki ......................... 435/94
7,000,000 B1   2/2006 O'Brien

OTHER PUBLICATIONS

International Search Report, Corresponding International Patent Application No. PCT/US2012/070715, E. I. Du Pont De Nemours and Company, mailed May 23, 2013.
Related U.S. Appl. No. 13/719,260, Caimi et al., filed Dec. 19, 2012.
Related International Patent Application, PCT Application No. PCT/US2012/070729, E. I. Dupont De Nemours and Company, (filed Dec. 19, 2012).
International Search Report, Related International Patent Application, PCT Application No. PCT/US2012/070729, E . I. Dupont De Nemours and Company, Mailed Mar. 1, 2013.
Acree, The Chemistry of Sugars in Boric Acid Solutions, Adv. Chem, American Chemical Society: Washington, DC (1973), pp. 208-219.
Pollak et al., Calorimetric Study of the Interactions of D-Glucose, D-Fructose, Sucrose and Poly(Vinyl Alcohol) With Borate Ions, Carbohydrate Research, vol. 241 (1993), pp. 279-283.
Robyt et al., Stereochemistry Involved in the Mechanism of Action of Dextransucrase in the Synthesis of Dextran and the Formation of Acceptor Products, Bioorganic Chemistry, vol. 11 (1982), pp. 115-132.
Simpson et al., Four Glucosyltransferases, GTFJ, GTFK, GTFL, and GTFM, From *Streptococcus salivarious* ATCC 25975, Microbiology, vol. 141 (1995), pp. 1451-1460.
Valdivia et al., Dextran Synthesis in the Presence of Oxianions, Annals of the New York Academy of Sciences, Wiley-Blackwell Publishing, Inc., US., vol. 542 (1988), pp. 390-394.
Valdivia et al., Effect of Borate Ions on Dextransucrase Acceptor Reaction, Biotechnology Letters, vol. 9, No. 1 (1987), pp. 1-6.

* cited by examiner

*Primary Examiner* — Nashaat Nashed

(57) ABSTRACT

A process for production of poly (α 1, 3 glucan) from a renewable feedstock, for applications in fibers, films, and pulps. The effect of addition of boric acid in increasing the yield of the desired end products, poly (α 1, 3 glucan) and fructose, and decreasing formation of the undesired by-product leucrose.

24 Claims, 2 Drawing Sheets

SEQUENCE LISTING

<160> NUMBER OF SEQ ID NOS: 6

<210> SEQ ID NO 1
<211> LENGTH: 34
<212> TYPE: DNA
<213> ORGANISM: Artificial sequence
<220> FEATURE:
<223> OTHER INFORMATION: Forward PCR primer for the Streptococcus sobrinus gtf-I gene

<400> SEQUENCE: 1
gggaattccc aggttgacgg taaatattat tact          34

<210> SEQ ID NO 2
<211> LENGTH: 34
<212> TYPE: DNA
<213> ORGANISM: Artificial sequence
<220> FEATURE:
<223> OTHER INFORMATION: Reverse PCR primer for the Streptococcus sobrinus gtf-I gene

<400> SEQUENCE: 2
agatctagtc ttagttccag ccacggtaca tacg                    34

<210> SEQ ID NO 3
<211> LENGTH: 1435
<212> TYPE: PRT
<213> ORGANISM: Streptococcus sobrinus

<400> SEQUENCE: 3

Gln Val Asp Gly Lys Tyr Tyr Tyr Asp Gln Gly Asn Val Lys
1               5                   10                  15

Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
            35                  40                  45

Ser Ala Val Ser Gln Asn Ala Thr Ile Phe Ala Ala Asn Asn Arg Ala
        50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys

```
            305                 310                 315                 320
        Asn Ala Asn Asn His Val Ser Ile Val Glu Ala Trp Ser Asp Asn Asp
                        325                 330                 335

Thr Pro Tyr Leu His Asp Asp Gly Asp Asn Leu Met Asn Met Asp Asn
                        340                 345                 350

Lys Phe Arg Leu Ser Met Leu Trp Ser Leu Ala Lys Pro Leu Asp Lys
                        355                 360                 365

Arg Ser Gly Leu Asn Pro Leu Ile His Asn Ser Leu Val Asp Arg Glu
                        370                 375                 380

Val Asp Asp Arg Glu Val Glu Thr Val Pro Ser Tyr Ser Phe Ala Arg
        385                 390                 395                 400

Ala His Asp Ser Glu Val Gln Asp Ile Ile Arg Asp Ile Ile Lys Ala
                        405                 410                 415

Glu Ile Asn Pro Asn Ser Phe Gly Tyr Ser Phe Thr Gln Glu Glu Ile
                        420                 425                 430

Glu Gln Ala Phe Lys Ile Tyr Asn Glu Asp Leu Lys Lys Thr Asp Lys
                        435                 440                 445

Lys Tyr Thr His Tyr Asn Val Pro Leu Ser Tyr Thr Leu Leu Leu Thr
                        450                 455                 460

Asn Lys Gly Ser Ile Pro Arg Val Tyr Tyr Gly Asp Met Phe Thr Asp
        465                 470                 475                 480

Asp Gly Gln Tyr Met Ala Asn Lys Thr Val Asn Tyr Asp Ala Ile Glu
                        485                 490                 495

Ser Leu Leu Lys Ala Arg Met Lys Tyr Val Ser Gly Gly Gln Ala Met
                        500                 505                 510

Gln Asn Tyr Gln Ile Gly Asn Gly Glu Ile Leu Thr Ser Val Arg Tyr
                        515                 520                 525

Gly Lys Gly Ala Leu Lys Gln Ser Asp Lys Gly Asp Ala Thr Thr Arg
                        530                 535                 540

Thr Ser Gly Val Gly Val Val Met Gly Asn Gln Pro Asn Phe Ser Leu
        545                 550                 555                 560

Asp Gly Lys Val Val Ala Leu Asn Met Gly Ala Ala His Ala Asn Gln
                        565                 570                 575

Glu Tyr Arg Ala Leu Met Val Ser Thr Lys Asp Gly Val Ala Thr Tyr
                        580                 585                 590

Ala Thr Asp Ala Asp Ala Ser Lys Ala Gly Leu Val Lys Arg Thr Asp
                        595                 600                 605

Glu Asn Gly Tyr Leu Tyr Phe Leu Asn Asp Asp Leu Lys Gly Val Ala
                        610                 615                 620

Asn Pro Gln Val Ser Gly Phe Leu Gln Val Trp Val Pro Val Gly Ala
        625                 630                 635                 640

Ala Asp Asp Gln Asp Ile Arg Val Ala Ala Ser Asp Thr Ala Ser Thr
                        645                 650                 655

Asp Gly Lys Ser Leu His Gln Asp Ala Ala Met Asp Ser Arg Val Met
                        660                 665                 670

Phe Glu Gly Phe Ser Asn Phe Gln Ser Phe Ala Thr Lys Glu Glu Glu
                        675                 680                 685

Tyr Thr Asn Val Val Ile Ala Asn Asn Val Asp Lys Phe Val Ser Trp
                        690                 695                 700

Gly Ile Thr Asp Phe Glu Met Ala Pro Gln Tyr Val Ser Ser Thr Asp
        705                 710                 715                 720

Gly Gln Phe Leu Asp Ser Val Ile Gln Asn Gly Tyr Ala Phe Thr Asp
                        725                 730                 735
```

-continued

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
        915                 920                 925

Ala Ser Phe Ile Thr Glu Ala Gly Asn Leu Tyr Tyr Phe Gly Lys Asp
    930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
            980                 985                 990

Gly Tyr Gln Gln Phe Gly Asn Asp Trp Arg Tyr Phe Lys Asp Gly Asn
        995                 1000                1005

Met Ala Val Gly Leu Thr Thr Val Asp Gly Asn Val Gln Tyr Phe
    1010                1015                1020

Asp Lys Asp Gly Val Gln Ala Lys Asp Lys Ile Ile Val Thr Arg
    1025                1030                1035

Asp Gly Lys Val Arg Tyr Phe Asp Gln His Asn Gly Asn Ala Ala
    1040                1045                1050

Thr Asn Thr Phe Ile Ala Asp Lys Thr Gly His Trp Tyr Tyr Leu
    1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Gln Gln Val Lys Gly Asp
    1085                1090                1095

Phe Val Thr Ser Asp Glu Gly Lys Leu Tyr Phe Tyr Asp Val Asp
    1100                1105                1110

Ser Gly Asp Met Trp Thr Asp Thr Phe Ile Glu Asp Lys Ala Gly
    1115                1120                1125

Asn Trp Phe Tyr Leu Gly Lys Asp Gly Ala Ala Val Thr Gly Ala
    1130                1135                1140

```
Gln Thr Ile Arg Gly Gln Lys Leu Tyr Phe Lys Ala Asn Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asp Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
    1265                1270                1275

Val Thr Gly Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Thr Phe Lys Asp Gly Ser Asp Ile Arg Phe Tyr Ser
    1325                1330                1335

Met Glu Gly Gln Leu Val Thr Gly Ser Gly Trp Tyr Glu Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Tyr Phe Gly Asn Asp Gly Ala
    1415                1420                1425

Arg Ile Tyr Arg Gly Trp Asn
    1430                1435

<210> SEQ ID NO 4
<211> LENGTH: 1342
<212> TYPE: PRT
<213> ORGANISM: Streptococcus salivarius

<400> SEQUENCE: 4

Met Asn Ile Asp Gly Lys Tyr Tyr Val Asn Glu Asp Gly Ser His
1               5                   10                  15

Lys Glu Asn Phe Ala Ile Thr Val Asn Gly Gln Leu Leu Tyr Phe Gly
                20                  25                  30

Lys Asp Gly Ala Leu Thr Ser Ser Thr Tyr Ser Phe Thr Pro Gly
            35                  40                  45

Thr Thr Asn Ile Val Asp Gly Phe Ser Ile Asn Asn Arg Ala Tyr Asp
            50                  55                  60
```

```
Ser Ser Glu Ala Ser Phe Glu Leu Ile Asp Gly Tyr Leu Thr Ala Asp
 65                  70                  75                  80

Ser Trp Tyr Arg Pro Ala Ser Ile Ile Lys Asp Gly Val Thr Trp Gln
                 85                  90                  95

Ala Ser Thr Ala Glu Asp Phe Arg Pro Leu Leu Met Ala Trp Trp Pro
                100                 105                 110

Asn Val Asp Thr Gln Val Asn Tyr Leu Asn Tyr Met Ser Lys Val Phe
                115                 120                 125

Asn Leu Asp Ala Lys Tyr Ser Ser Thr Asp Lys Gln Glu Thr Leu Lys
                130                 135                 140

Val Ala Ala Lys Asp Ile Gln Ile Lys Ile Glu Gln Lys Ile Gln Ala
145                 150                 155                 160

Glu Lys Ser Thr Gln Trp Leu Arg Glu Thr Ile Ser Ala Phe Val Lys
                165                 170                 175

Thr Gln Pro Gln Trp Asn Lys Glu Thr Glu Asn Tyr Ser Lys Gly Gly
                180                 185                 190

Gly Glu Asp His Leu Gln Gly Gly Ala Leu Leu Tyr Val Asn Asp Ser
                195                 200                 205

Arg Thr Pro Trp Ala Asn Ser Asp Tyr Arg Arg Leu Asn Arg Thr Ala
210                 215                 220

Thr Asn Gln Thr Gly Thr Ile Asp Lys Ser Ile Leu Asp Glu Gln Ser
225                 230                 235                 240

Asp Pro Asn His Met Gly Gly Phe Asp Phe Leu Leu Ala Asn Asp Val
                245                 250                 255

Asp Leu Ser Asn Pro Val Val Gln Ala Glu Gln Leu Asn Gln Ile His
                260                 265                 270

Tyr Leu Met Asn Trp Gly Ser Ile Val Met Gly Asp Lys Asp Ala Asn
                275                 280                 285

Phe Asp Gly Ile Arg Val Asp Ala Val Asp Asn Val Asp Ala Asp Met
                290                 295                 300

Leu Gln Leu Tyr Thr Asn Tyr Phe Arg Glu Tyr Tyr Gly Val Asn Lys
305                 310                 315                 320

Ser Glu Ala Asn Ala Leu Ala His Ile Ser Val Leu Glu Ala Trp Ser
                325                 330                 335

Leu Asn Asp Asn His Tyr Asn Asp Lys Thr Asp Gly Ala Ala Leu Ala
                340                 345                 350

Met Glu Asn Lys Gln Arg Leu Ala Leu Leu Phe Ser Leu Ala Lys Pro
                355                 360                 365

Ile Lys Glu Arg Thr Pro Ala Val Ser Pro Leu Tyr Asn Asn Thr Phe
                370                 375                 380

Asn Thr Thr Gln Arg Asp Glu Lys Thr Asp Trp Ile Asn Lys Asp Gly
385                 390                 395                 400

Ser Lys Ala Tyr Asn Glu Asp Gly Thr Val Lys Gln Ser Thr Ile Gly
                405                 410                 415

Lys Tyr Asn Glu Lys Tyr Gly Asp Ala Ser Gly Asn Tyr Val Phe Ile
                420                 425                 430

Arg Ala His Asp Asn Asn Val Gln Asp Ile Ile Ala Glu Ile Ile Lys
                435                 440                 445

Lys Glu Ile Asn Pro Lys Ser Asp Gly Phe Thr Ile Thr Asp Ala Glu
                450                 455                 460

Met Lys Gln Ala Phe Glu Ile Tyr Asn Lys Asp Met Leu Ser Ser Asp
465                 470                 475                 480
```

-continued

```
Lys Lys Tyr Thr Leu Asn Asn Ile Pro Ala Ala Tyr Ala Val Met Leu
                485                 490                 495

Gln Asn Met Glu Thr Ile Thr Arg Val Tyr Tyr Gly Asp Leu Tyr Thr
            500                 505                 510

Asp Asp Gly His Tyr Met Glu Thr Lys Ser Pro Tyr Tyr Asp Thr Ile
            515                 520                 525

Val Asn Leu Met Lys Ser Arg Ile Lys Tyr Val Ser Gly Gly Gln Ala
        530                 535                 540

Gln Arg Ser Tyr Trp Leu Pro Thr Asp Gly Lys Met Asp Asn Ser Asp
545                 550                 555                 560

Val Glu Leu Tyr Arg Thr Asn Glu Val Tyr Thr Ser Val Arg Tyr Gly
                565                 570                 575

Lys Asp Ile Met Thr Ala Asn Asp Thr Glu Gly Ser Lys Tyr Ser Arg
            580                 585                 590

Thr Ser Gly Gln Val Thr Leu Val Ala Asn Asn Pro Lys Leu Asn Leu
        595                 600                 605

Asp Gln Ser Ala Lys Leu Asn Val Glu Met Gly Lys Ile His Ala Asn
    610                 615                 620

Gln Lys Tyr Arg Ala Leu Ile Val Gly Thr Ala Asp Gly Ile Lys Asn
625                 630                 635                 640

Phe Thr Ser Asp Ala Asp Ala Ile Ala Ala Gly Tyr Val Lys Glu Thr
                645                 650                 655

Asp Ser Asn Gly Val Leu Thr Phe Gly Ala Asn Asp Ile Lys Gly Tyr
            660                 665                 670

Glu Thr Phe Asp Met Ser Gly Phe Val Ala Val Trp Val Pro Val Gly
            675                 680                 685

Ala Ser Asp Asn Gln Asp Ile Arg Val Ala Pro Ser Thr Glu Ala Lys
        690                 695                 700

Lys Glu Gly Glu Leu Thr Leu Lys Ala Thr Glu Ala Tyr Asp Ser Gln
705                 710                 715                 720

Leu Ile Tyr Glu Gly Phe Ser Asn Phe Gln Thr Ile Pro Asp Gly Ser
                725                 730                 735

Asp Pro Ser Val Tyr Thr Asn Arg Lys Ile Ala Glu Asn Val Asp Leu
            740                 745                 750

Phe Lys Ser Trp Gly Val Thr Ser Phe Glu Met Ala Pro Gln Phe Val
        755                 760                 765

Ser Ala Asp Asp Gly Thr Phe Leu Asp Ser Val Ile Gln Asn Gly Tyr
        770                 775                 780

Ala Phe Ala Asp Arg Tyr Asp Leu Ala Met Ser Lys Asn Asn Lys Tyr
785                 790                 795                 800

Gly Ser Lys Glu Asp Leu Arg Asp Ala Leu Lys Ala Leu His Lys Ala
                805                 810                 815

Gly Ile Gln Ala Ile Ala Asp Trp Val Pro Asp Gln Ile Tyr Gln Leu
            820                 825                 830

Pro Gly Lys Glu Val Val Thr Ala Thr Arg Thr Asp Gly Ala Gly Arg
        835                 840                 845

Lys Ile Ala Asp Ala Ile Ile Asp His Ser Leu Tyr Val Ala Asn Ser
850                 855                 860

Lys Ser Ser Gly Lys Asp Tyr Gln Ala Lys Tyr Gly Gly Glu Phe Leu
865                 870                 875                 880

Ala Glu Leu Lys Ala Lys Tyr Pro Glu Met Phe Lys Val Asn Met Ile
                885                 890                 895

Ser Thr Gly Lys Pro Ile Asp Asp Ser Val Lys Leu Lys Gln Trp Lys
```

-continued

Ala Glu Tyr Phe Asn Gly Thr Asn Val Leu Glu Arg Gly Val Gly Tyr
    900             905                 910

Val Leu Ser Asp Glu Ala Thr Gly Lys Tyr Phe Thr Val Thr Lys Glu
    915             920                 925

Gly Asn Phe Ile Pro Leu Gln Leu Thr Gly Lys Glu Lys Val Ile Thr
930             935                 940

Gly Phe Ser Ser Asp Gly Lys Gly Ile Thr Tyr Phe Gly Thr Ser Gly
    945             950                 955             960

Thr Gln Ala Lys Ser Ala Phe Val Thr Phe Asn Gly Asn Thr Tyr Tyr
            965                 970                 975

Phe Asp Ala Arg Gly His Met Val Thr Asn Ser Glu Tyr Ser Pro Asn
        980                 985                 990

Gly Lys Asp Val Tyr Arg Phe Leu Pro Asn Gly Ile Met Leu Ser
    995                 1000                1005

Asn Ala Phe Tyr Ile Asp Ala Asn Gly Asn Thr Tyr Leu Tyr Asn
    1010                1015                1020

Ser Lys Gly Gln Met Tyr Lys Gly Gly Tyr Thr Lys Phe Asp Val
    1025                1030                1035

Ser Glu Thr Asp Lys Asp Gly Lys Glu Ser Lys Val Val Lys Phe
    1040                1045                1050

Arg Tyr Phe Thr Asn Glu Val Met Ala Lys Gly Val Thr Val
    1055                1060                1065

Ile Asp Gly Phe Thr Gln Tyr Phe Gly Glu Asp Gly Phe Gln Ala
    1070                1075                1080

Lys Asp Lys Leu Val Thr Phe Lys Gly Lys Thr Tyr Tyr Phe Asp
    1085                1090                1095

Ala His Thr Gly Asn Gly Ile Lys Asp Thr Trp Arg Asn Ile Asn
    1100                1105                1110

Gly Lys Trp Tyr Tyr Phe Asp Ala Asn Gly Val Ala Ala Thr Gly
    1115                1120                1125

Ala Gln Val Ile Asn Gly Gln Lys Leu Tyr Phe Asn Glu Asp Gly
    1130                1135                1140

Ser Gln Val Lys Gly Gly Val Val Lys Asn Ala Asp Gly Thr Tyr
    1145                1150                1155

Ser Lys Tyr Lys Glu Gly Phe Gly Glu Leu Val Thr Asn Glu Phe
    1160                1165                1170

Phe Thr Thr Asp Gly Asn Val Trp Tyr Tyr Ala Gly Ala Asn Gly
    1175                1180                1185

Lys Thr Val Thr Gly Ala Gln Val Ile Asn Gly Gln His Leu Tyr
    1190                1195                1200

Phe Asn Ala Asp Gly Ser Gln Val Lys Gly Gly Val Val Lys Asn
    1205                1210                1215

Ala Asp Gly Thr Tyr Ser Lys Tyr Asn Ala Ser Thr Gly Glu Arg
    1220                1225                1230

Leu Thr Asn Glu Phe Phe Thr Thr Gly Asp Asn Asn Trp Tyr Tyr
    1235                1240                1245

Ile Gly Ala Asn Gly Lys Ser Val Thr Gly Glu Val Lys Ile Gly
    1250                1255                1260

Asp Asp Thr Tyr Phe Phe Ala Lys Asp Gly Lys Gln Val Lys Gly
    1265                1270                1275

Gln Thr Val Ser Ala Gly Asn Gly Arg Ile Ser Tyr Tyr Tyr Gly
    1280                1285                1290

```
Asp Ser Gly Lys Arg Ala Val Ser Thr Trp Ile Glu Ile Gln Pro
    1310                1315                1320

Gly Val Tyr Val Tyr Phe Asp Lys Asn Gly Leu Ala Tyr Pro Pro
    1325                1330                1335

Arg Val Leu Asn
    1340

<210> SEQ ID NO 5
<211> LENGTH: 4327
<212> TYPE: DNA
<213> ORGANISM: Streptococcus sobrinus

<400> SEQUENCE: 5
gggaattccc aggttgacgg taaatattat tactacgacc aagatggcaa tgttaagaaa      60
aactttgctg tcagcgttgg tgataagatt tattactttg atgaaactgg cgcttacaag     120
gacactagca aggttgatgc cgacaagtcc agttcagctg taagtcaaaa tgcaacaata     180
tttgcagcta ataaccgtgc ctacagcacc tcagctaaaa attttgaagc cgttgataac     240
tacctgacag ctgactcttg gtatcgtcca aaatcaatcc tgaaagacgg aaaaacttgg     300
acagaatctg gcaaagatga cttccgcccg cttctcatgg cttggtggcc tgataccgaa     360
accaaacgta actacgttaa ttacatgaac aaggttgttg gtattgataa gacctatacc     420
gctgaaacga gccaagctga tttaacggca gcagcagaat tggttcaagc tcgtattgaa     480
caaaaaatta caagtgaaaa taacactaag tggctccgtg aggcgatttc tgcctttgtg     540
aaaactcagc cgcaatggaa tggtgaaagc gaaaagcctt acgatgatca cttgcaaaat     600
ggtgctcttc tctttgacaa tcaaactgat ttaacaccag atacgcaatc gaactatcgt     660
ttgctcaatc gcacaccaac taaccaaact ggttccttgg attctcgttt cacctataac     720
ccaaatgacc cactgggcgg ctatgatttc cttttagcca acgatgttga taattccaat     780
ccagtcgtgc aagcggaaca actcaactgg ctgcactacc tgctgaactt tggctctatc     840
tatgccaatg atgcagatgc caattttgac tcaatccgtg tagatgcggt tgataatgtt     900
gatgctgacc ttctgcaaat ctctagtgat taccttaagg cagcttacgg tattgataaa     960
aacaacaaaa atgctaataa ccacgtttct atcgtagaag catggagcga caacgatacc    1020
ccttatctcc atgatgatgg cgacaacctc atgaacatgg acaacaagtt ccgtttgtct    1080
atgctttggt ctttggctaa accattggac aaacgttctg gcttgaatcc cctcatccac    1140
aacagtctgg ttgaccgtga ggttgatgac cgtgaggttg aaactgttcc aagttacagc    1200
tttgctcggg ctcatgatag cgaagttcag gatatcattc gtgatattat taaggctgag    1260
attaatccaa attcatttgg ttattcattc acccaagaag aaattgaaca agctttcaag    1320
atttacaacg aagatctcaa gaagactgat aaaaaataca ctcactacaa tgtgccgctc    1380
tcttacaccc tgcttctcac aaacaagggc tctatcccac gtgtctacta tggagatatg    1440
ttcaccgatg atggccaata catggctaat aagactgtga actacgatgc tatcgaatca    1500
ctcctaaagg ctcgtatgaa gtacgtttca ggtggtcagg ctatgcaaaa ttaccaaatc    1560
ggtaatggcg aaatcttgac ttctgtccgt tatggtaagg gtgcccttaa acaaagcgat    1620
aagggtgatg cgacaactcg tacgtcaggt gtcggcgttg ttatgggaaa ccaacccaac    1680
tttagcttgg atggaaaggt tgtagcccct aacatgggtg ctgcccacgc taaccaagaa    1740
taccgtgctc ttatggtatc aactaaagac ggtgttgcaa cctatgctac agatgctgat    1800
gctagcaagg ctggtctggt taagcgcaca gatgaaaatg gttacctcta cttcttgaac    1860
```

```
gacgatctca aggggggttgc taaccctcag gtttctggtt tccttcaagt ctgggtacca  1920
gtgggagcag cagatgacca agatattcgt gtagcagcta gcgatacagc aagtaccgat  1980
ggaaaatcac tccatcaaga tgctgctatg gactctcgcg tcatgtttga aggtttctct  2040
aacttccaat cttttgcgac aaaagaagaa gagtatacca atgttgttat tgctaacaat  2100
gttgataaat ttgtttcatg gggaatcact gactttgaaa tggctcctca gtatgtctca  2160
tctactgacg gtcagttcct tgactctgtc attcaaaatg ttatgcctt taccgaccgt  2220 tatgacttgg gtatgtctaa agcaaacaag tatggtacag ccgaccaatt ggttaaggct  2280
atcaaggctc tccatgctaa aggcctgaag gttatggcag actgggttcc agaccaaatg  2340
tacaccttcc ctaaacaaga agtggtcact gttactcgga cagataagtt tggcaaacca  2400
atcgcaggaa gccaaattaa tcacagtctc tacgtaacag atacaaagag ctctggtgat  2460
gactatcaag ctaaatacgg cggtgccttc cttgacgaat aaaggaaaaa atatccagaa  2520
ctctttacca agaaacaaat ctctactggt caggcgattg atccatctgt taagattaaa  2580
caatggtctg ctaagtactt taatggaagt aatattcttg gccggggtgc cgattatgtc  2640
ctcagcgacc aagtcagcaa caagtacttc aacgttgcca gcgatacact cttcttacca  2700
agcagcttac tcggcaaggt tgtagagtct ggtattcgtt atgatggtaa gggttatatt  2760
tataactcaa gtgcaactgg tgaccaagtc aaagcaagct tcattaccga agcaggcaat  2820
ctatactact tcggtaaaga cggttatatg gtgactggcg ctcaaaccat taatggtgct  2880
aactatttct tccttgaaaa tggtacggct cttcgcaaca ctatttatac agatgctcaa  2940
ggcaatagcc attactacgc aaatgacggt aaacgctatg aaaatggtta ccaacaattt  3000
ggtaatgact ggcgttactt caaggacggt aatatggccg ttggcttgac aactgttgat  3060
ggcaatgttc aatactttga taaagatggt gttcaagcta aggataagat tattgtcacc  3120
cgtgatggta aggttcgtta ctttgaccaa cataatggaa atgctgcaac caataccttc  3180
atcgctgaca agactggtca ctggtactat ctaggtaaag atggtgtcgc tgttaccggt  3240
gctcaaaccg ttgggaaaca aaaactttac tttgaagcaa acggtcaaca agttaagggt  3300
gacttcgtaa cttctgacga aggtaaactt tacttctacg atgtcgattc aggtgacatg  3360
tggactgata ccttcattga agataaggca ggcaattggt tctaccttgg taaagatggt  3420
gcagctgtga ctggtgctca aactattcgt ggccaaaaac tttacttcaa ggctaacggc  3480
caacaagtca aggagatat cgtcaagggt actgatggta agatccgtta ctacgacgct  3540
aaatctggtg aacaagtctt caacaagact gttaaggccg ctgatggcaa gacctatgtt  3600
atcggaaatg atggcgttgc ggttgatcca agcgttgtca aggacaaaac cttcaaggat  3660
gcttcaggtc tcttcgtttt ctataacctc aaaggacaac tggtaacagg cagcggttgg  3720
tatgaaactg caaatcacga ttgggttta tccaatctg gtaaagcctt gactggggaa  3780
cagaccatca tggtcaaca tctttacttc aaggaagatg gacatcaagt caaaggacaa  3840
ctggtaacag gaactgatgg taaggttcgc tattatgatg caaattcagg cgaccaagcc  3900
ttcaacaagt ctgtaacagt taacggtaag acttactact tcggtaatga tggcactgct  3960
caaacagcgg gaaatcctaa gggacaaacc ttcaaagatg gttcagatat ccgcttttac  4020
agcatggaag gccaattagt gactggcagt ggttggtacg aaaacgcaca aggtcagtgg  4080
ctctatgtga aaaatggtaa agtcttgaca ggcctgcaaa cagttggtag ccaacgtgtt  4140
tactttgacg aaaatggtat tcaagccaaa ggtaaagcag taagaacttc cgacggtaag  4200
```

```
atacgctact tcgatgaaaa ttcaggtagc atgattacca accaatggaa attcgtttac    4260
ggtcaatatt attacttcgg taatgatggc gcacgtatct accgtggctg gaactaagac    4320
tagatct                                                              4327

<210> SEQ ID NO 6
<211> LENGTH: 4049
<212> TYPE: DNA
<213> ORGANISM: Streptococcus salivarius

<400> SEQUENCE: 6
gggaattcca tatgaacatt gatggtaaat attactatgt taatgaagat ggttcacaca      60
aagaaaactt tgccattact gtaaatggtc aattgcttta cttcggtaaa gatggtgctc     120
ttacaagttc atcaacatac tctttcacac caggaacaac aaatattgtt gatggtttct     180
caataaataa ccgtgcctac gattcatctg aagctagctt tgaattgatt gatggttatt     240
tgactgcaga tagctggtac cgtccagctt ctatcatcaa agatggtgta acttggcaag     300
catcaactgc agaagatttc cgtccacttt tgatggcttg gtggccaaat gtagatacac     360
aagttaacta cttgaactac atgtctaaag tatttaactt ggatgctaaa tattcaagta     420
cagataagca agaaactttg aaagttgctg ctaaggacat tcaaatcaag attgagcaaa     480
agattcaggc tgaaaaatca acacaatggt tgcgtgaaac tatctctgcc tttgttaaga     540
cacaaccaca atggaacaaa gaaactgaaa actactctaa aggtggcggc gaagatcacc     600
ttcaaggtgg tgcccttctt tatgtgaatg attcacgtac accatgggcg aattctgact     660
atcgtcgttt gaaccgtaca gcaactaacc agactggtac aattgataaa tcaattcttg     720
atgagcaatc agatccaaac cacatgggtg gtttcgactt cttgctagct aatgacgtag     780
atttgtcaaa cccagttgtt caagcggaac aattgaacca aatccactac cttatgaact     840
ggggttcaat cgttatgggt gacaaggatg ctaacttcga tggtatccgt gtcgacgcgg     900
tagataatgt cgatgcagac atcttcaact ctacacaaac tacttccgtg agtactatgg     960
tgttaacaaa tctgaagcaa cgctcttgc tcacatctca gtccttgaag catggagcct    1020
taatgacaac cactacaatg acaagacaga tggcgctgcg cttgctatgg aaaacaaaca    1080
acgtttggct ctcctcttct cattggctaa accaatcaaa gaacgtacac cagctgtaag    1140
tcctttgtat aacaatactt tcaacacgac acaacgtgat gaaagactg attggattaa    1200 caaagatgga agcaaggcct ataacgaaga cggaacagtt aaacagtcta caatcggtaa    1260
atataacgag aaatacggag atgcgtcagg aaattacgtc tttatccgtg cccatgataa    1320
caacgttcaa gatattattg ctgaaatcat caagaaagaa atcaatccaa atcagatgg    1380 tttcacgatt actgatgctg aaatgaagca agcctttgag atttacaaca agacatgct    1440 cagcagcgac aaaaaatata cgcttaacaa catcccagcg gcttacgcgg ttatgttgca    1500
aaacatggaa actatcactc gtgtctacta tggagacctt tatacagatg atggtcacta    1560
catggaaact aagtctccat attacgatac cattgttaac ttgatgaaga gtcgtatcaa    1620
gtatgtatct ggtgggcaag cacaacgttc atactggttg ccaactgatg gtaagatgga    1680
caattcagat gttgaacttt accgcacaaa tgaagtctac acttcagtac gttatggtaa    1740
agacattatg acagctaatg atacagaagg ttctaaatac agccgtactt ctggtcaggt    1800
aacacttgta gctaacaatc caaaattgaa ttttggatcaa tcagctaaac ttaatgttga    1860
aatgggtaaa atccatgcca accaaaaata ccgtgctttg attgttggta cagctgatgg    1920
tatcaagaac tttacatctg atgcagatgc aatcgcagca ggttacgtta aagaaacaga    1980
```

-continued

```
cagcaacggt gtcttgactt tcggtgctaa tgacatcaag ggttatgaaa catttgatat    2040
gtctggtttc gtagcagttt gggttccagt tggagcttca gataatcaag atatccgagt    2100
agcgccttca acagaagcta aaaaagaggg tgaattgact cttaaagcga ctgaagctta    2160
tgattcacaa ttaatctacg aaggcttctc taactttcaa actattccag atggttcaga    2220
tccttcagtc tatactaacc gtaagattgc tgaaaatgtt gatttgttca aatcatgggg    2280
tgtaacatca tttgaaatgg cacctcaatt tgtatctgct gacgatggta ccttccttga    2340
ctcagttatc caaaatggtt atgcctttgc agaccgttac gatcttgcca tgagtaagaa    2400
caataaatac ggttctaaag aagatctacg tgatgctctt aaagcacttc ataaggctgg    2460
tattcaagca atcgctgact gggttccaga ccaaatttac caattgccag gtaaagaagt    2520
tgtaacagcg actcgtactg atggtgctgg tcgtaagatt gcggacgcta tcattgacca    2580
ctcactttat gtggctaact ctaagtcatc aggcaaagat taccaagcta atacggtgg    2640 tgaattcttg gctgaactta agctaagta ccctgaaatg ttcaaggtaa acatgatttc    2700
aactggtaaa ccaattgatg attctgttaa attgaaacaa tggaaggctg aatacttcaa    2760
cggaacaaac gttcttgaac gtggtgttgg ctatgtactt agcgatgaag caactggtaa    2820
gtatttcact gtcactaaag aaggtaactt cattcctctt caattgacag gtaaagaaaa    2880
ggttattact ggattctcaa gtgatggtaa aggaatcact tacttcggta caagtggtac    2940
acaagctaaa tctgcctttg taaccttcaa tggtaacact tactactttg atgctcgtgg    3000
tcacatggtt actaacagtg aatactcacc aaatggtaaa gacgtttatc gtttcttacc    3060
aaatggtatc atgttgagta atgccttcta cattgatgct aatggtaata cctacctta    3120 taactctaaa ggtcaaatgt acaagggtgg ttacactaaa tttgatgttt ctgaaactga    3180
taaagacggt aaagaatcta aggttgtgaa attccgttac ttcactaatg aaggtgtcat    3240
ggccaaaggt gttacggtta ttgatggttt cacacaatat tttggagaag acggtttcca    3300
agctaaagat aagttagtaa cctttaaagg taaaacttat tactttgacg cacacactgg    3360
taatggtatc aaggatactt ggagaaatat caatggtaag tggtactact ttgatgcaaa    3420
cggtgttgct gctacaggtg cacaagtcat caatggtcaa aaactttact tcaatgaaga    3480
tggaagccaa gttaaaggtg gcgttgttaa gaatgcagat ggtacttaca gcaagtacaa    3540
agaaggtttt ggagagctag tgactaacga attcttcaca actgatgca atgtttggta    3600 ctatgcaggc gctaatggta agactgttac aggtgcacaa gtcatcaatg ccaacacct    3660 atactttaat gcagacggaa gccaagttaa gggtggtgtt gttaagaatg cagatggtac    3720
ttatagtaag tataatgctt caacaggtga acgcttgact aatgagtttt tcacaacagg    3780
cgacaacaac tggtactaca ttggtgctaa tggtaagtca gtgactggtg aagttaaaat    3840
tggtgacgat acttatttct tcgctaagga tggtaaacaa gtaaaaggtc aaacagtaag    3900
tgctggcaat ggtcgaatta gctattacta tggtgatagt ggtaagagag ctgttagcac    3960
atggatagaa attcaaccag gagtttacgt ttactttgat aagaatggtc ttgcttatcc    4020
acctagagtg ctaaactaag actagatct                                      4049
```

INCREASED POLY (α 1, 3 GLUCAN) YIELD USING BORIC ACID

CROSS-REFERENCE TO RELATED APPLICATIONS

This application claims the benefit of priority to U.S. Provisional Application No. 61/577,274, filed on Dec. 19, 2011.

FIELD OF INVENTION

This invention relates to the field of production of a polysaccharide. Specifically, it relates to production of poly (α 1, 3 glucan) via an enzymatic reaction. More specifically, it relates to increasing the titer of poly (α 1, 3 glucan) formed during the enzymatic reaction.

BACKGROUND

Cellulose, a polysaccharide consisting of β (1, 4)-linked glucose, formed by natural processes, (Applied Fiber Science, F. Happey, Ed., Chapter 8, E. Atkins, Academic Press, New York, 1979) has become the preeminent fiber for use in manufactured textiles, films and resins. Cotton, an especially pure form of naturally occurring cellulose, is well-known for its beneficial attributes in textile applications.

Cellulosic fibers such as cotton and rayon increasingly present sustainability issues with respect to land use and environmental imprint. This may be a significant factor leading to increased level of research into textiles containing polyester fiber blends with cellulosic materials and more sustainable solutions for cellulosic-derived materials. It is highly desirable, therefore, to discover other glucose-based polysaccharides for application in films, fibers and resins that can be economically produced from renewable resources. In addition such polymers offer materials that are environmentally benign throughout their entire life cycle.

Poly (α 1, 3 glucan), a glucan polymer characterized by having α (1, 3) glycoside linkages, has been isolated by contacting an aqueous solution of sucrose with a glycosyl-transferase (gtfJ) enzyme isolated from *Streptococcus salivarius* (Simpson et al., Microbiology, 141: 1451-1460, 1995). Poly (α 1, 3 glucan) refers to a polysaccharide composed of D-glucose monomers linked by glycosidic bonds. Films prepared from poly (α 1, 3 glucan) tolerate temperatures up to 150° C. and provide an advantage over polymers obtained from β (1, 4) linked polysaccharides (Ogawa et al., Fiber Differentiation Methods, 47: 353-362, 1980).

U.S. Pat. No. 7,000,000 disclosed preparation of a polysaccharide fiber comprising hexose units, wherein at least 50% of the hexose units within the polymer were linked via α (1, 3) glycoside linkages using the gtfJ enzyme. The gtfJ enzyme utilizes sucrose as a substrate in a polymerization reaction producing poly (α 1, 3 glucan) and fructose as end-products (Simpson et al., et al., Microbiology, 141: 1451-1460, 1995).

Production of low-cost poly (α 1, 3 glucan) derived from sucrose, for commercial applications, requires a high yield process producing minimal undesirable by-products. In addition to poly (α 1, 3 glucan), the other end product, fructose, is also a desirable product due to its application as a high value sweetener. However, fructose is also known to compete with glucose, acting as an acceptor in the gtf enzyme reaction thus hindering conversion of available glucose to poly (α 1, 3 glucan) and limiting the final titer of poly (α 1, 3 glucan) (Valdivia et al., (Ann. NY Acad. Sci. 542:390-394, 1988).

Robyt and Eklund (Bioorganic Chemistry, 11: 115-132, 1982) and Prat, D, et al., (Biotechnol. Letters, 9: 1-6, 1987) reported production of a by-product leucrose, a disaccharide of glucose and fructose with α (1, 5) linkages, as well as fructose, by the dextranase enzyme of *Leuconostoc mesenteroides* when sucrose was used as substrate. Dextranase enzymes (E.G. 2.4.1.2) belong to glycosyltransferases family of enzymes and catalyze α (1, 4) and α (1, 6) type glycoside linkages.

Boric acid is known to react with suitable diol containing compounds (e.g., carbohydrates) in aqueous solution, to produce borate esters (T. Acree, Adv. Chem.; Am. Chem. Soc.: Washington, D.C., pp 208-219, 1973). The suitability of a diol for reaction with boric acid is determined by oxygen-oxygen bond distance (2.49 A to 2.63 A) within the diol and oxygen-carbon-carbon-oxygen dihedral angle (<40°). Fructose, in the furanose form, is an excellent configuration for bond distance and dihedral angle compared to glucose or sucrose for reaction with boric acid. Thus, the equilibrium constant for ester formation with boric acid favors fructose over glucose or sucrose in solution (Pollak, V. and Mlynek, J.; Carbohydrate Research, 241: 279-283, 1993). The relatively tight association between fructose and borate can be used to sequester this carbohydrate in a solution containing other sugars. Sequestration of fructose prevents its use as an acceptor in the dextranase reaction resulting in reduced leucrose synthesis. Prat et al., (supra) and Valdivia et al., (supra) described altering the yield of end products in a dextranase reaction by adding sodium tetraborate under strict conditions including specific concentrations of sodium tetraborate (<110 mM) and at pH<7.0. In the presence of 60 mM sodium tetraborate and at pH 7.0, the dextranase enzyme used by Prat et al., (supra) showed no activity at all.

Interaction between boric acid, borate anions and tetraborate occurs with carbohydrates having a specific configuration (Pollak, and Mlynek, supra). It is not clear whether a similar interaction can occur between borate and poly (α 1, 3 glucan). Furthermore, it has been shown that tetraborate dramatically reduces the activity of *Leuconostoc mesenteroides* dextranase, which belongs to a family of enzymes that catalyze α (1, 4) and α (1, 6) type glycoside linkages. It is not known if similar effects can be observed with the general class of glycosyltransferases which produce a high percentage of α (1,3) glycosyl linkages.

Commercial production of poly (α 1, 3 glucan) and fructose from sucrose, using glycosyltransferases, requires development of methods to increase the yield of these products during the enzymatic reaction.

SUMMARY OF INVENTION

This invention is a process for production of poly (α 1, 3 glucan) from a renewable feedstock, for applications in fibers, films, and pulps. The effect of addition of boric acid in increasing the yield of the desired end products and decreasing undesired by-product leucrose formation is disclosed.

In one aspect, the disclosed invention is a reaction solution for the synthesis of poly (α 1, 3 glucan) comprising:
  a) at least one gtf enzyme;
  b) boric acid; and
  c) sucrose,
whereby poly (α 1, 3 glucan) is produced with a lower concentration of leucrose by-product than is produced in the absence of boric acid.

In another aspect, the disclosed invention is an improved process for producing (α 1, 3 glucan) having a reduced concentration of leucrose as by-product comprising the steps:

a) providing a reaction solution comprising:
   i) at least one gtf enzyme;
   ii) boric acid; and
   iii) sucrose;
wherein sucrose is converted by the enzyme to poly (α 1, 3 glucan) and fructose and wherein the amount of the by-product leucrose formed in the conversion is less than 35% of the sucrose consumed.

DESCRIPTION OF FIGURES AND DNA SEQUENCES

NUCLEOTIDE SEQUENCES

Figure 1:
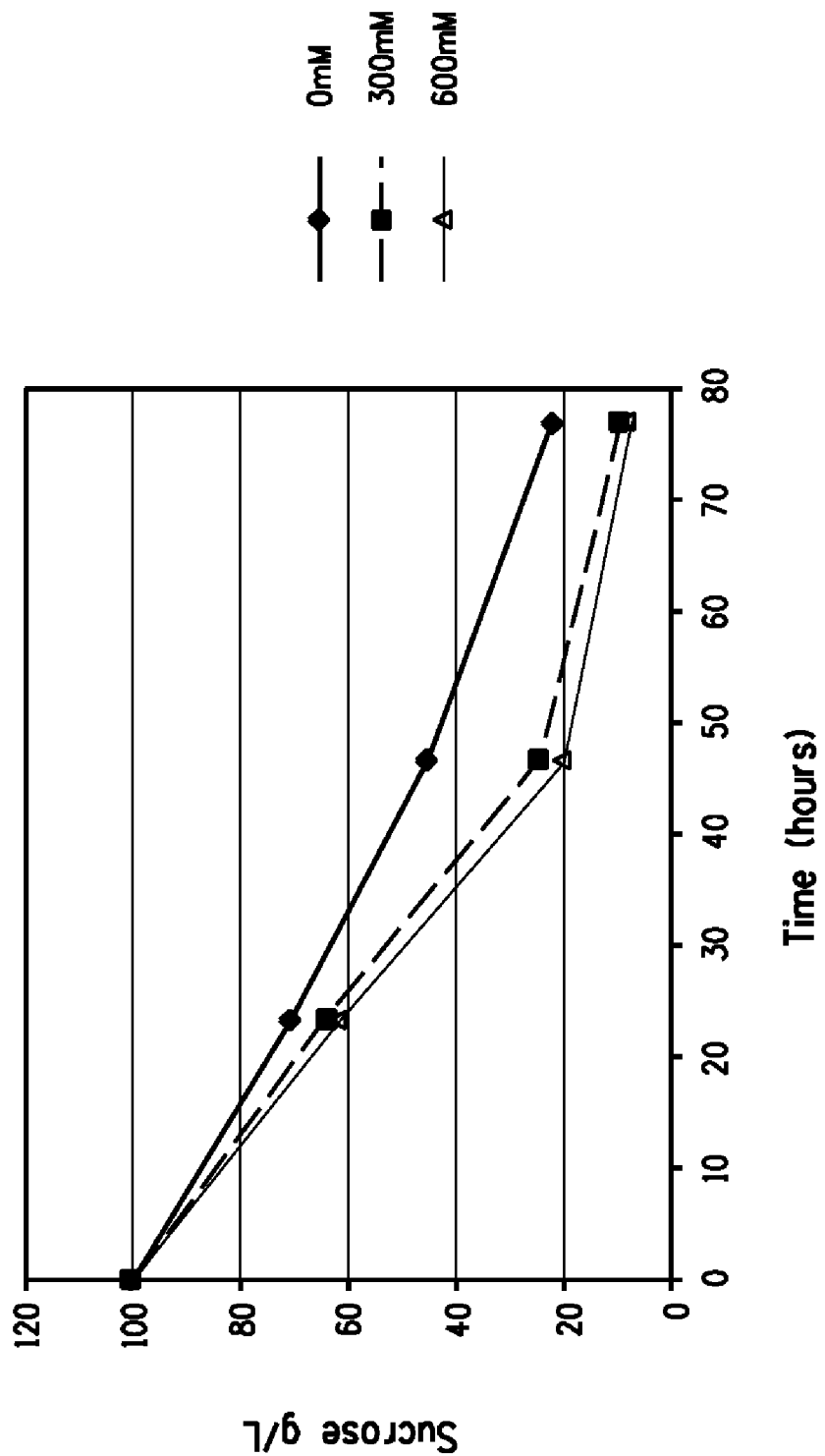
FIG. 1 is a graph of gtfJ enzyme (SEQ ID NO:4) reaction solutions containing no boric acid (black diamonds); 300 mM boric acid (black squares) and 600 mM boric acid (black triangles). Sucrose concentration is shown on the X axis and time (hours) is shown on the Y axis.
Figure 2:
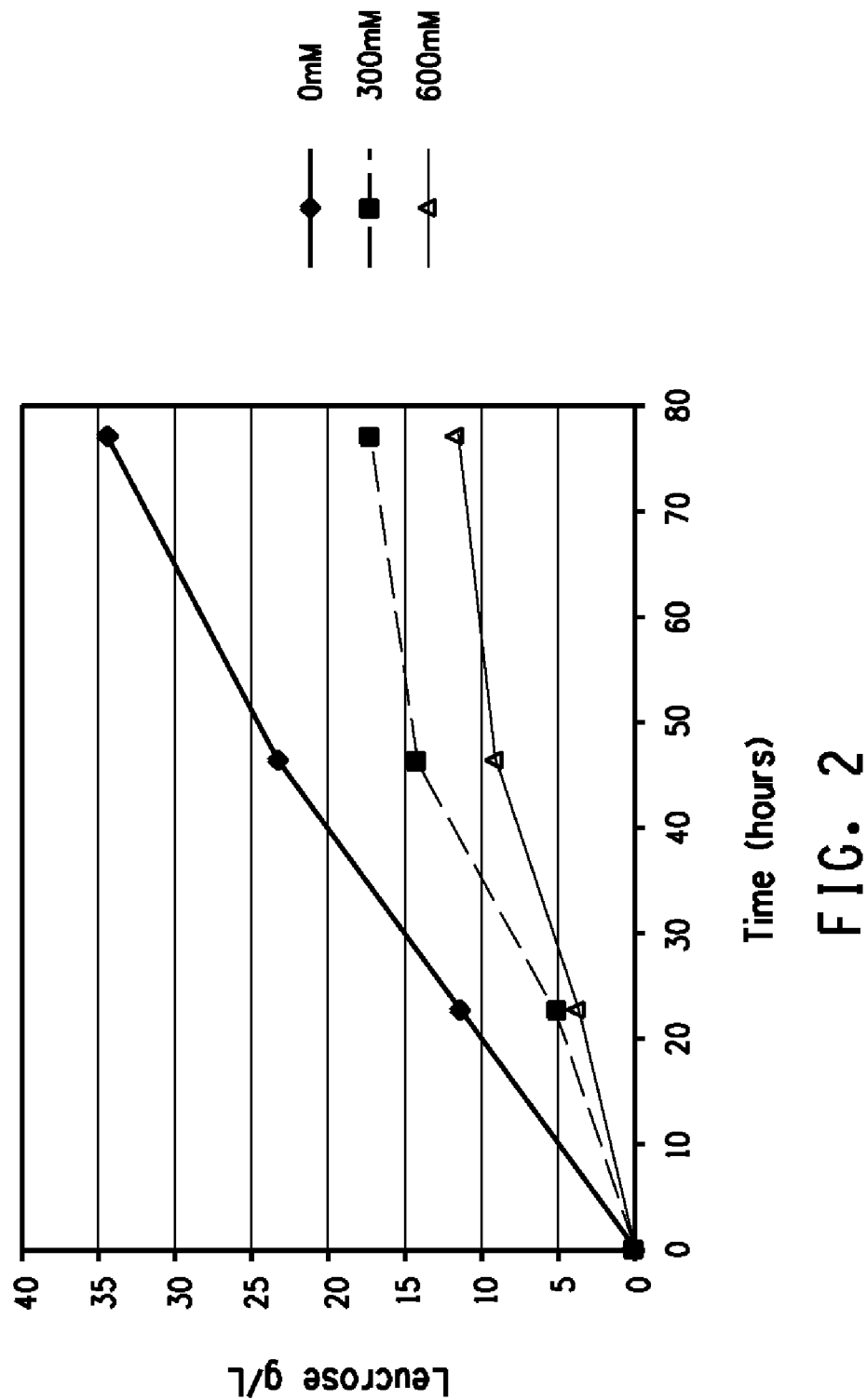
FIG. 2 is a graph showing changes in leucrose concentration in the FIG. 1 reaction solutions containing no boric acid (black diamonds); 300 mM boric acid (black squares) and 600 mM boric acid (black triangles).

SEQ ID NO. 1—is the nucleotides sequence of the forward PCR primer of *S. sobrinus* gtfI gene (BAA02976)

GGGAATTCCCAGGTTGACGGTAAATATTATTACT

SEQ ID NO. 2—is the nucleotides sequence of the reverse PCR primer *S. sobrinus* gtfI gene, (BAA02976).

AGATCTAGTCTTAGTTCCAGCCACGGTACATACG

SEQ ID NO. 3—Amino acid sequence (amino acid 162 to 1597) for *Streptococcus sobrinus* gtfJ (Genbank accession number BAA02976).
SEQ ID NO. 4—is the amino acid sequence (amino acid 178 to 1518) for *Streptococcus salivarius* gtfJ (Genbank accession number Z11873).
SEQ ID NO. 5—is the coding sequence (base 466 to base 4773) for *Streptococcus sobrinus* gtfI, (Genbank accession number BAA02976).
SEQ ID NO. 6—is the coding sequence (base 532 to base 4557) for *Streptococcus salivarius* gtfJ, (Genbank accession number Z11873).

DETAILED DESCRIPTION OF INVENTION

Poly (α 1, 3 glucan) is a potentially low cost polymer which can be enzymatically produced from renewable resources such as sucrose using the gtfJ enzyme (e.g., SEQ ID NO:4) of *Streptococcus salivarius*. The present invention describes formation of by-products poly (α 1, 3 glucan), fructose and leucrose in gtf enzyme reactions and the effect of boric acid in increasing fructose formation and decreasing leucrose formation.

The term "glycosyltransferase (gtf) enzyme", as used herein, refers to an enzyme excreted by oral streptococci, such as *Streptococcus salivarius* which utilizes the high free energy of the glycosidic bond of sucrose to synthesize poly (α 1, 3 glucan). A glycosidic bond can join two monosaccharides to form a disaccharide. The glycosidic bonds can be in the α or β configuration and can generate, for example, α (1, 2), α (1, 3), α (1, 4), α (1, 6), β (1, 2), β (1, 3), β (1, 4) or β (1, 6) linkages. The term "α (1,3) glycoside linkage", as used herein, refers to a type of covalent bond that joins glucose molecules to each other through the ring carbons 1 and 3 on adjacent glucose rings.

The term "poly (α 1, 3 glucan)", as used herein, refers to high molecular weight, linear polymers obtained from polysaccharide molecules resulting from linking glucose units via α (1,3) glycosidic linkages.

The present invention relates to a process for increasing the titer of the polysaccharide, poly (α 1, 3 glucan) and fructose and decreasing the titer of the undesired by-product, leucrose, in an enzymatic reaction solution using sucrose as the substrate and one or more gtf enzymes. The term "enzymatic reaction" refers to a reaction that is performed by the gtf enzyme. An "enzyme reaction solution" of the present invention generally refers to a reaction mixture comprising at least one gtf enzyme in a buffer solution comprising sucrose and possibly one or more primers to convert sucrose to poly (α 1, 3 glucan).

The glycosyltransferase enzyme used in the present invention can be any gtf enzyme. The gtf enzyme used can be from any streprococci. Suitable gtf enzymes can be, for example, the gtfJ of *Streptococcus salivarius* (e.g., SEQ ID NO:4), the gtfB and the gtfC from *Streptococcus mutans*, the gtfI of *Streptococcus sobrinus* (e.g., SEQ ID NO:3) and the gtfI from *Streptococcus downei*. Particularly, the *Streptococcus* species can be *Streptococcus salivarius*. More particularly, the gtf enzyme can be the gtfJ (E.C. 2.4.1.5) enzyme of *Streptococcus salivarius* (e.g., SEQ ID NO:4). Alternatively, the gtfI enzyme of *Streptococcus sobrinus* (e.g., SEQ ID NO:3) can be used.

In one embodiment, the enzyme reaction solution can comprise only one gtf enzyme as described herein. In another embodiment, the enzyme reaction solution can comprise a combination of more than one type of gtf enzyme.

For purposes of this invention, sufficient quantities of the gtfJ enzyme (e.g., SEQ ID NO:4) can be produced using a recombinant *E. coli* strain expressing the desired gtfJ enzyme (e.g., SEQ ID NO:4). Methods for designing the codon optimized genes and expression in *E. coli* are well known in the art. The *E. coli* strain (DH10B) expressing gtfJ enzyme (e.g., SEQ ID NO:4) was prepared as described in the commonly owned U.S. Pat. No. 7,000,000.

Methods for the growth of recombinant microorganisms are well known in the art. Recombinant microorganisms expressing the desired gtf enzyme to perform the instant reaction can be grown in any container, such as, for example: various types of flasks with and without indentations; any container that can be sterilized and sealed and temperature-controlled; or any type of fermenter. In one embodiment, production of the gtfJ enzyme (e.g., SEQ ID NO:4) for poly (α 1, 3 glucan) production in the present invention can be achieved by growing the recombinant *E. coli* DH10B, expressing the gtfJ enzyme (e.g., SEQ ID NO:4), in a fermenter.

The gtfJ enzyme of *Streptococcus salivarius* (e.g., SEQ ID NO:4), used as the catalyst for conversion of sucrose to poly (α 1, 3 glucan) in the current invention, is a primer-independent gtf enzyme. The primer-independent enzymes do not require the presence of a primer to perform the reaction. A primer-dependent gtf enzyme as referenced in the present application refers to a gtf enzyme that requires the presence of an initiating molecule in the enzyme reaction solution to act as a primer for the enzyme during poly (α 1, 3 glucan) synthesis. Thus a "primer", as the term is used herein, refers to any molecule that can act as the initiator for the primer-dependent glycosyltransferases. For the purposes of the present invention, either or both a primer-independent enzyme, and/or a primer-dependent gtf enzyme can be used in the same enzyme reaction system during poly (α 1, 3 glucan) synthesis.

While gtfJ (e.g., SEQ ID NO:4) is a primer-independent enzyme, it also acts with primer. In the present invention, dextran, which is a complex, branched glucan was used as a primer for the gtfJ enzyme (e.g., SEQ ID NO:4). In addition to dextran other carbohydrate-based primers can be used in the gtf reaction of the current invention. In one embodiment, the primer can be from any low to med molecular weight (2,000-50,000 Dalton) glucose-based carbohydrate.

In another embodiment, the primer in the reaction solution can be hydrolyzed poly (α 1, 3 glucan). In another embodiment, the primer in the reaction solution can be from any low to med (340-50,000 Dalton) non-glucose-based carbohydrate. In another embodiment, the primer in the reaction solution can be from any combination of any low to med molecular weight glucose-based carbohydrate. In another embodiment, the primer is glucose.

The production of poly (α 1, 3 glucan), by the gtfJ enzyme of *Streptococcus salivarius* (e.g., SEQ ID NO:4), is inhibited by its end product, fructose. When fructose accumulates in the enzyme reaction solution it can inhibit poly (α 1, 3 glucan) production, presumably by competing for available glycosyl moieties and thus results in the formation of the undesirable by-product disaccharide, leucrose.

Boric acid can be used to sequester fructose in a solution containing other sugars. The sequestration of fructose prevents its use as an acceptor in the gtf reaction and therefore results in reduced leucrose synthesis. The term "sequestration of fructose", as used herein, refers to formation of a tight association between fructose and boric acid thus preventing fructose from reacting with gtf to produce the undesirable by-product, leucrose.

In one embodiment, the yield of sucrose can be increased by decreasing the formation of leucrose to less than 75% of the amount of leucrose formed in the absence of boric acid. In another embodiment, the amount of leucrose formed in the presence of boric acid can be less than one-half the amount of leucrose formed in the absence of boric acid. In still another embodiment, the amount of leucrose formed in the presence of boric acid can be less than one-third the amount formed in the absence of boric acid. In still another embodiment, the amount of leucrose formed in the presence of boric acid can be less than one-tenth the amount formed in the absence of boric acid.

In one embodiment, the concentration of boric acid used in the gtfJ (e.g., SEQ ID NO:4) reaction can be from 100 millimolar (mM) to 600 mM. In another embodiment, the concentration of boric acid can be from 300 mM to 600 mM.

In another embodiment the concentration of poly (α 1, 3 glucan) in the enzymatic reaction solution is increased from 0.08 grams poly (α 1, 3 glucan) per gram of sucrose to 0.25 grams poly (α 1, 3 glucan) per gram of sucrose.

In one embodiment concentration of fructose in the enzymatic reaction solution is increased from 29% to 43% of sucrose converted.

Other materials that can be used in place of boric acid to sequester fructose can include, but may not be limited to: 2-Aminopyrimidine-5-boronic acid; Benzene-1,4-diboronic acid; Carboxyphenylboronic acid; Fluorene-2-boronic acid; Furan-2-boronic acid; Naphthalene-1-boronic acid; Nitrophenylboronic acid; n-Pentylboronic acid; Methylpropylboronic acid; Methoxyphenylboronic acid; and Phenylboronic acid, for example.

In the present invention, the effect of pH of the gtf enzyme reaction solution can be from 6.5 to 8.1. In one embodiment the pH of the gtf enzyme reaction solution is 7.75. In another embodiment, the pH of the gtf enzyme reaction solution is 8.1.

EXAMPLES

The invention is further described but not limited by the following specific embodiments thereof.

Materials

T10 dextran (D9260), Isopropyl β-D-1-thiogalactopyranoside (IPTG) (I6758) and boric acid (B1934) were obtained from Sigma, St. Louis, Mo.

Whatman-1 filter paper was obtained from Whatman Filters, Maidstone Kent, UK.

Solenoid driven micro-valve was from Bio-Chem Fluidics, Boonton, N.J.

Bellco spin flask was from Bellco, Vineland, N.J.

VWR Ag/AgCL pH probe was from VWR International, Radnor, Pa.

Eutech pH/ORP controller was from division of Thermo Fisher Scientific Inc., Waltham, Mass.

Luria broth (LB) medium was from Becton, Dickinson and Company, Franklin Lakes, N.J.

The bead beater was obtained from MP Biomedicals, Eschwege, Germany).

Eppendorf 5415D Centrifuge was from Eppendorf, Hamburg, Germany)

Protein concentration in samples were determined using the Coomassie Plus, Bradford Assay Kit (Thermo Scientific, Rockford, Ill.)

High pressure chromatography (HPLC) was performed using a 1200 series, Agilent, Santa Clara Calif.) instrument. The column used for analysis was an Aminex HPX-87C column, (Bio-Rad Laboratories, Hercules, Calif.) which was maintained at 85° C. using a flow rate of 0.6 milliliters per minute (mL/min) with water as the mobile phase. HPLC analysis was used to determine disappearance of sucrose and the accumulation of fructose, glucose and leucrose. Using this system the following retention times were observed for chemicals of interest: sucrose (8.29 minutes, min); leucrose (9.40 min); glucose (10.12 min) and fructose (12.89 min).

Example 1

Preparation of Crude Extracts of GtfJ (Seq Id No:4)

The gtfJ gene of *S. salivarius* is available in Genbank (Genbank accession number Z11873, SEQ ID NO. 4). To produce sufficient quantities of gtfJ (SEQ ID NO:4), a truncated gtfJ gene (SEQ ID NO. 6) was expressed in *E. coli* strain (DH10B) as described in the commonly owned U.S. Pat. No. 7,000,000. *E. coli* (DH10B), cells expressing the gtfJ enzyme (SEQ ID NO:4), were grown in the LB medium (10 grams per liter, g/L Tryptone; 5 g/L yeast extract; and 10 g/L NaCl). *E. coli* cells were inoculated to an initial optical density (OD at $600_{nm}$) of 0.025 and were allowed to grow at 37° C. in an incubator while shaking at 250 rpm. The cultures were then induced by addition of 1 mM IPTG when they reached an OD of 0.8-1.0. Induced cultures were left on the shaker and harvested 3 hours post induction. The cells were removed by centrifugation (25° C., 16,000 rpm) using an Eppendorf centrifuge and cell pellets were suspended in 0.01 volume of 5.0 mM phosphate buffer (pH 7.0) and cooled to 4° C. on ice. The cells were broken using a bead beater with 0.1 millimeters (mm) silica beads. The broken cells were centrifuged at 16,000 rpm at 4° C. to precipitate the unbroken cells and cell debris. The crude extract (containing soluble gtfJ enzyme, SEQ ID NO:4) thus obtained contained 2.9 milligram per milliliter (mg/mL) of protein as determined by the Bradford protein assay.

Example 2

Effect of Boric Acid Addition on the Amount of Product Formed by GtfJ (Seq Id No:4)

To determine the effect of boric acid addition on the yield of poly (α 1,3 glucan) enzyme reactions were performed in 50 mL reactors in the presence (test) or absence (control) of boric acid.

GtfJ (SEQ ID NO:4) reaction solutions contained sucrose (50-150 g/L); potassium phosphate buffer (10 mM); T10-dextran primer at a final concentration of 1 g/L; and total soluble enzyme (0.4-1.0 volume percent, v %). Reactions were performed at 25° C.-35° C. in the presence or absence of boric acid. Concentration of sucrose, leucrose, fructose and glucose were determined using HPLC. The yield of poly (α1, 3 glucan) was determined by measuring its dry weight after filtration and washing with 8 volumes of water and then drying for 48 hours at 35° C.

In one experiment, the reaction solution contained: sucrose (150 g/L); gtfJ enzyme (SEQ ID NO:4) (0.4 volume %) and T-10 dextran primer (1 g/L). The initial pH of the reaction solution was adjusted to 7.5 using phosphate buffer. The temperature was held at 30° C. and the reaction solution was left stationary for 51 hours. Boric acid (at either 300 mM or 600 mM concentrations) was added to the reaction solution and the pH was adjusted to 7.5 using sodium hydroxide, prior to gtfJ (SEQ ID NO:4) addition. The pH of the reaction solution was monitored throughout the test, but was not adjusted. The pH of reactions containing boric acid continued to drop from the initial adjusted pH, while the pH of the control reaction solution, without boric acid, did not change throughout the experiment.

Addition of boric acid into gtfJ (SEQ ID NO:4) reaction solution decreased the leucrose concentration by approximately 2 to 3-fold (Table 1). Additionally, the yield of poly (α1, 3 glucan) recovered in this reaction increased relative to the control reaction that did not contain any boric acid. The concentration of fructose was also proportionally higher in reactions containing boric acid.

As the reaction progressed, pH dropped and leucrose continued to accumulate suggesting that controlling the pH of the gtfJ (SEQ ID NO:4) reaction containing boric acid can potentially affect by-product synthesis.

TABLE 1

Effect of boric acid on gtfJ reaction product formation

| Grams/liter | Control | 300 mM Boric acid | 600 mM Boric acid |
| --- | --- | --- | --- |
| Initial sucrose | 153.28 | 155.34 | 152.88 |
| End sucrose | 16.16 | 6.68 | 8.96 |
| Leucrose | 58.85 | 29.95 | 21.06 |
| Glucose | 10.13 | 14.75 | 16.98 |
| Fructose | 45.15 | 64.19 | 69.32 |
| % Sucrose used | 89 | 96 | 94 |
| Leucrose (% of sucrose) | 43 | 20 | 15 |
| Glucose (% of sucrose) | 7 | 10 | 12 |
| Fructose (% of sucrose) | 33 | 43 | 48 |
| Yield g poly (α 1, 3 glucan)/g sucrose) | 0.17 | 0.29 | 0.37 |

To study the effect of lower (i.e., less than 300 mM) concentrations of boric acid on leucrose formation in an experiment, either 100 mM or 200 mM of boric acid was used in the reaction solution. The reaction solutions contained sucrose (100 g/L), gtfJ (SEQ ID NO:4) (0.5 v %), T-10 dextran primer (1 g/L) and potassium phosphate buffer, (10 mM). The initial pH of the reaction was 7.0. The temperature of the reaction was held at 27° C. for 44 hours. Initial boric acid concentration in the reactions was 0 mM (control), 100 mM (pH adjusted with KOH or NaOH) or 200 mM (NaOH adjusted). The results listed in Table 2 indicate that presence of boric acid in the enzyme reaction solution reduced leucrose formation relative to the control reaction. Counter ions (potassium or sodium) used for initial pH adjustment did not affect leucrose formation.

TABLE 2

Effect of reduced concentration of boric acid on product formation during gtfJ reaction in the presence of counter ions

| Grams/Liter | Control | (Na) 100 mM boric acid | (K) 100 mM boric acid | (Na) 200 mM boric acid |
| --- | --- | --- | --- | --- |
| Initial sucrose | 112.12 | 111.36 | 114.57 | 102.36 |
| End sucrose | 14.21 | 7.23 | 7.17 | 7.48 |
| Leucrose | 37.50 | 28.60 | 29.68 | 25.74 |
| Glucose | 6.56 | 8.86 | 8.98 | 9.11 |
| Fructose | 28.64 | 36.41 | 37.32 | 37.53 |
| % Sucrose used | 87 | 94 | 94 | 93 |
| Leucrose (% of sucrose) | 38 | 27 | 28 | 27 |
| Glucose (% of sucrose) | 7 | 9 | 8 | 10 |
| Fructose (% of sucrose) | 29 | 35 | 35 | 40 |

In summary, the data presented in this Example demonstrate that the addition of boric acid to gtfJ enzyme (SEQ ID NO:4) reaction solutions resulted in an increase in poly (α 1, 3 glucan) yield which corresponded to a decrease in leucrose accumulation.

Example 3

Effect of Boric Acid on Sucrose Uptake by GtfJ (Seq Id No:4)

To determine if the presence of boric acid affected sucrose conversion and hence poly(α1,3 glucan) formation by gtfJ (SEQ ID NO:4), reaction solutions were prepared containing sucrose (100 g/L), gtfJ (SEQ ID NO:4) (0.5 volume %) boric acid (either 300 mM or 600 mM) and potassium phosphate buffer, (10 mM); at an initial pH of 7.0. The control reaction was set up with similar ingredients but without any boric acid.

The reaction was monitored over time. Samples were taken at intervals and the concentration of soluble sugars was determined by HPLC analysis as described in Example 1. Results for sucrose use over time are shown in FIG. 1a. From the data, it is clear that the rate of sucrose use is higher for a reaction containing 300 mM boric acid relative to the control (no boric acid). Furthermore, the reaction with the highest boric acid concentration (600 mM) resulted in the highest sucrose use rate. Thus the presence of boric acid in above experiments resulted in an increased rate of conversion of sucrose to poly (α1, 3 glucan).

The concentration of leucrose continuously increased in an enzyme reaction solution containing 100 g/L sucrose, where the initial pH had been adjusted to 7.4 using potassium phosphate buffer (10 mM final concentration)(FIG. 1B). The data provides additional evidence that the presence of boric acid results in reduced synthesis of leucrose over time. Measuring pH of the control reaction solution during the experiment demonstrated only a slight drop in pH from 7.4 to 7.2 at the end of the experiment (77 hours). In contrast to the control, the pH drop was much more pronounced in both reactions containing boric acid. The pH in the 300 mM boric acid reaction solution decreased from 7.4 to 5.98 and the pH in the 600 mM reaction was at pH 5.60 at the end of the experiment.

Example 4 pH Controlled Enzyme Reactions Containing Boric Acid

To perform this experiment, a 150 ml capacity Bellco spin flask was used and the pH of the reaction solution was monitored using a VWR Ag/AgCL pH probe which was linked to a Eutech pH/ORP controller set to maintain pH at 7.5. Base was delivered to the reaction using a solenoid driven microvalve from a reservoir containing 2.0 M sodium hydroxide. The gtfJ (SEQ ID NO:4) reaction solutions contained: sucrose (100 g/L); gtfJ (SEQ ID NO:4) (0.5 volume %), T-10 dextran primer (1 g/L) and boric acid at 300 mM in each reaction. Initial reaction pH was 7.5. The reactions were performed at 25° C. for 56 hours.

The data shown in Table 3 compares sucrose consumption and product synthesis in gtfJ enzyme (SEQ ID NO:4) reaction solutions, containing 300 mM boric acid, with or without pH control.

TABLE 3

Effect of pH control in substrate consumption and product formation

| Grams/Liter | Control reaction | pH Adjusted reaction |
|---|---|---|
| Initial sucrose | 105.51 | 105.79 |
| End sucrose | 66.77 | 35.13 |
| Leucrose | 7.74 | 3.10 |
| Glucose | 5.08 | 13.77 |
| Fructose | 12.76 | 30.38 |
| % sucrose used | 37 | 67 |
| Leucrose (% of sucrose) | 20 | 4 |
| Glucose (% of sucrose) | 13 | 19 |
| Fructose (% of sucrose) | 33 | 43 |

The results indicate that maintaining the pH at 7.5 during the gtfJ (SEQ ID NO:4) reaction was far more effective in reduction of leucrose formation in the presence of boric acid. At approximately reaction mid-point, the concentration of leucrose in the pH adjusted flask accounted for only 4% of the sucrose converted. The level of leucrose at the end of the reaction (94% of sucrose converted) increased to 5% of sucrose used in the pH controlled test. The concentration of Leucrose in the control reaction was 20% of converted sucrose at the same time-point and increased to 27% at completion of the experiment. In addition to the reduced by-product accumulation, the pH controlled reaction used twice as much sucrose relative to the control.

Since maintaining the pH of a reaction was shown to be an effective method for reducing leucrose accumulation the effect of controlling the pH of the reaction at higher pH than 7.5 was investigated. The reaction solutions contained: sucrose (100 g/L); gtfJ (SEQ ID NO:4) (0.5 v %); T-10 dextran primer (1 g/L) and boric acid (300 mM). One reaction was maintained at pH 7.75 and the other one was maintained at pH 8.1. The reaction solutions were maintained at 25° C. for 76 hours.

Table 4 shows the concentration of leucrose formed at the end of these reactions at 11% and 6% respectively. When the results obtained in these experiments are compared to those obtained in reactions with no pH control (e.g. Table 1, when leucrose accounts for 20% of sucrose used) it becomes apparent that leucrose formation in a gtfJ (SEQ ID NO:4) reaction can be more effectively reduced when pH of the reaction solution is effectively controlled.

TABLE 4

Effect of pH 7.75 and 8.1 on sucrose consumption and product formation in a gtfJ reaction solution

| Grams/Liter | pH 7.75 | pH 8.1 |
|---|---|---|
| Initial sucrose | 114.40 | 114.36 |
| End sucrose | 4.55 | 3.55 |
| Leucrose | 12.16 | 6.61 |
| Glucose | 12.56 | 14.91 |
| Fructose | 46.34 | 48.16 |
| % sucrose used | 96 | 97 |
| Leucrose (% of sucrose) | 11 | 6 |
| Glucose (% of sucrose) | 11 | 13 |
| Fructose (% of sucrose) | 42 | 43 |

Example 5

Cloning and Expression of the Gtf Enzyme of Streptococcus Sobrinus (Seq Id No:3)

To examine the effect of boric acid on sucrose consumption and product formation in a gtf reaction performed by an alternative gtf enzyme, the gtfI gene from *Streptococcus sobrinus* (Genbank accession number BAA02976, SEQ ID NO. 3) was cloned using methods well known in the art.

A truncated version of the *S. sobrinus* 6715 gene coding for gtfI protein (SEQ ID NO:3) was isolated from (*S. sobrinus* ATCC 27351) (SEQ ID NO. 5) by PCR amplification using primers based on the gene sequence described in Genbank accession number BAA02976 and by Abo et al., (J. Bacteriol., 173: 998-996, 1991). PCR reactions were performed using a 5'-end primer (SEQ ID NO: 1) and a 3'-end primer (SEQ ID NO: 2).

In (SEQ ID NO:1) (5'GGGAATTCCCAGGTTGACGG-TAAATATTATTACT), the coding sequence corresponded to bases 466 through 491 of the gtfI gene of *S. sobrinus* ATCC 27351, and additionally provided the sequence for an Eco RI restriction enzyme site that was used for cloning purposes.

In (SEQ ID NO: 2) (5'-AGATCTAGTCTTAGTTCCAGC-CACGGTACATA) the coding sequence corresponded to the reverse compliment of bases 4749 through 4774 of *S. sobrinus* (ATCC 27351) gtfI gene. The reverse PCR primer also included the sequence for an XbaI site for cloning purposes. The PCR was performed by methods well-known in the art. All subsequent steps for preparation of *E. coli* expression vector for the gtfI gene (SEQ ID NO:5) were performed as recommended by the manufacturers of the products used.

The resulting PCR product was digested with Eco RI and Xba I restriction enzymes and then purified using a Promega PCR Clean-up kit (A9281, Promega, USA) as recommended by the manufacturer. The DNA fragment was ligated into an *E coli* protein expression vector (pET24a, Novagen, USA). The ligated reaction was transformed into the DE3 cell line (New England Biolabs, USA) and plated on solid LB medium (10 g/L, tryptone; 5 g/L yeast extract; 10 g/L NaCl; 14% agar; 100 μg/ml ampcillin) for selection of single colonies. Transformed *E. coli* cells were grown overnight in the LB medium. The cells were then diluted to an optical density (OD) of 0.025 ($A600_{nm}$) then grown to a density of 1.0 OD in the LB medium. At this density, IPTG (final concentration, 1.0 mM) was added to the culture to induce the gtfI gene (SEQ ID NO:5) expression. Cultures were incubated at 37° C. for an additional 2 to 4 hours before cell harvest. Cell disruption, total soluble protein isolation and enzyme reactions were carried out as described in Example 1.

Enzyme reaction solutions for investigating the effect of addition of boric acid on substrate consumption and product formation by gtfI (SEQ ID NO:3) contained: sucrose (100 g/L); gtfI (SEQ ID NO:3) (0.4 volume %); T-10 dextran primer (1 g/L). The control experiment did not have any boric acid. The test experiment included 100 mM boric acid. The Initial pH of the reaction solution was 7.5 using potassium phosphate. The reaction pH was monitored, but not adjusted after addition of enzyme. The temperature was held at 30° C. for 44 hours.

The effect of boric acid on reduction of the by-products formed using VI enzyme (SEQ ID NO:3) is summarized in Table 5. The data indicate that presence of boric acid in the gtfI (SEQ ID NO:3) reaction resulted in a 3 fold decrease in leucrose formation.

TABLE 5

Streptococcus sobrinus gtfI reaction

| Grams/Liter | 0 mm Boric acid | 100 mM Boric acid |
|---|---|---|
| Initial sucrose | 99.83 | 98.84 |
| End sucrose | 8.79 | 5.08 |
| Leucrose | 50.73 | 14.69 |
| Glucose | 5.32 | 8.55 |
| Fructose | 28.25 | 48.20 |
| % sucrose used | 91 | 95 |
| Leucrose (% of sucrose) | 56 | 16 |
| Glucose (% of sucrose) | 6 | 9 |
| Fructose (% of sucrose) | 31 | 51 |

Example 6 pH Controlled Enzyme Reactions Containing Boric with Dextran or Glucose as Primer To determine the effect of boric acid addition on the yield of poly (α 1, 3 glucan) enzyme reactions were performed in a 4 L jacketed glass resin kettle equipped with a glass agitator shaft with 3 glass turbine impellers was used. The pH of the reaction solution was monitored using a VWR Symphony gel epoxy flask combination electrode which was linked to a pH controller set (Cole-Parmer Digital Chemcadet pH meter/controller Model 5652-00) and maintained pH at 7.5. Base was delivered to the reaction using a Cole-Parmer, Masterflex, console drive pump, model #7521-40 pump from a reservoir containing 4.0 M sodium hydroxide. The gtfJ (SEQ ID NO:4) reaction solutions contained: sucrose (100 g/L); gtfJ (SEQ ID NO:4) (1.0 volume %), either T-10 dextran (1 g/L) or glucose (0.1 g/L) as a primer and boric acid at 300 mM in each reaction. Buffer system was 2.75 mM KCl, 2.75 mM $K_2SO_4$, and 0.75 mM potassium acetate. Initial pH of the reaction was 7.5 and the reactions were performed at 25° C. for 43-45 hours.

The gtf enzyme reactions were performed in the presence (test) or absence (control) of boric acid. The gtfJ (SEQ ID NO:4) control reaction solutions contained: sucrose (100 g/L); gtfJ (SEQ ID NO:4) (1.0 volume %), either T-10 dextran primer (1 g/L) or glucose (1.0 g/L) and 50 mM Potassium phosphate ($KH_2PO_4$) buffer pH was adjusted to 7.0 with 10% KOH solution. Reactions were incubated in an Innova 4200 incubator/shaker at 25° C. Concentration of products in the reaction solution was determined as described above.

The data shown in Table 6 compares sucrose consumption and product formation in gtfJ enzyme (SEQ ID NO:4) reaction solutions, with either glucose or dextran as a primer in pH-controlled experiments with or without borate.

TABLE 6

Effect of primer in substrate consumption and product formation

| g/L | No borate—dextran primed | No borate—glucose primed | Borate—pH control at 7.5—dextran primed | Borate—pH control at 7.5—glucose primed |
|---|---|---|---|---|
| Initial sucrose | 104.2 | 104.4 | 100.0 | 102.7 |
| End sucrose | 1.4 | 1.4 | 3.2 | 3.6 |
| Leucrose | 36.0 | 30.5 | 5.3 | 3.2 |
| Glucose | 5.1 | 5.0 | 12.8 | 11.9 |
| Fructose | 29.4 | 32.3 | 45.2 | 46.8 |
| % sucrose used | 99 | 99 | 97 | 97 |
| Leucrose (% of sucrose) | 35 | 30 | 5 | 3 |
| Glucose (% of sucrose) | 5 | 5 | 13 | 12 |
| Fructose (% of sucrose) | 29 | 31 | 47 | 47 |
| Yield of Glucan: G poly (α 1, 3 glucan)/g sucrose | 0.151 | 0.18 | 0.224 | 0.241 |

The results indicate that borate's effect on reducing leucrose and increasing poly (α 1, 3 glucan) formation is primer independent. The comparison with non-borate experiments also shows increased yield of poly (α 1, 3 glucan) with concomitant reduction in leucrose production.

What is claimed is:

1. A reaction solution for the synthesis of poly (alpha 1,3 glucan) comprising:
   a) at least one *Streptococcus* glucosyltransferase enzyme that synthesizes poly (alpha 1,3 glucan) from sucrose;
   b) boric acid; and
   c) sucrose,
whereby poly (alpha 1,3 glucan) is produced with a lower concentration of leucrose by-product than is produced in the absence of boric acid.

2. The reaction solution of claim 1 further comprising at least one primer.

3. The reaction solution of claim 2 wherein the primer is dextran.

4. The reaction solution of claim 2 wherein the primer is hydrolyzed poly (alpha 1,3 glucan).

5. The reaction solution of claim 1, wherein the *Streptococcus* glucosyltransferase enzyme is a *Streptococcus salivarius* glucosyltransferase enzyme or *Streptococcus sobrinus* glucosyltransferase enzyme.

6. The reaction solution of claim 5, wherein the *Streptococcus salivarius* glucosyltransferase enzyme comprises SEQ ID NO:4 and the *Streptococcus sobrinus* glucosyltransferase enzyme comprises SEQ ID NO:3.

7. The reaction solution of claim 5, wherein the reaction solution pH is maintained from 6.5 to 8.1.

8. The reaction solution of claim 7, wherein the concentration of boric acid in the reaction solution is from about 100 millimolar to about 600 millimolar.

9. The reaction solution of claim 8, wherein the concentration of boric acid in the reaction solution is from about 300 millimolar to about 600 millimolar.

10. The reaction solution of claim 2 wherein the enzyme of (a) is a primer dependent enzyme.

11. The reaction solution of claim 10 wherein the primer is glucose.

12. The reaction solution of claim 1 wherein the enzyme of (a) is a primer independent enzyme.

13. The reaction solution of claim 1 wherein more than one enzyme of (a) is present in the reaction solution.

14. The reaction solution of claim 13 wherein one glucosyltransferase enzyme is primer dependent and one glucosyltransferase enzyme is primer independent.

15. The reaction solution of claim 1 wherein the concentration of boric acid in the reaction solution is from about 100 millimolar to about 600 millimolar.

16. The reaction solution of claim 15, wherein the concentration of boric acid in the reaction solution is from about 300 millimolar to about 600 millimolar.

17. The reaction solution of claim 1 wherein the reaction solution pH is maintained from 6.5 to 8.1.

18. The reaction solution of claim 17, wherein the concentration of boric acid in the reaction solution is from about 300 millimolar to about 600 millimolar.

19. The reaction solution of claim 1 wherein the yield of poly (alpha 1,3 glucan) formed in the reaction solution improves from 0.08-0.1 g glucan/g sucrose to 0.25 g glucan/g sucrose.

20. A process for reducing the amount of byproduct leucrose formed during enzymatic synthesis of poly (alpha 1,3 glucan) comprising:
    providing a reaction solution comprising:
       i) at least one *Streptococcus* glucosyltransferase enzyme that synthesizes poly (alpha 1,3 glucan) from sucrose;
       ii) boric acid; and
       iii) sucrose;
    wherein the sucrose is converted to poly (alpha 1,3 glucan) and fructose and wherein the amount of leucrose produced in the conversion is less than 35% of the sucrose consumed.

21. The process of claim 20 wherein the yield of leucrose formed decreases from 44% sucrose to 4% of sucrose converted.

22. The process of claim 20 wherein the reaction solution pH is maintained from 6.5 to 8.1.

23. The process of claim 20 wherein the yield of fructose increases from 29% sucrose to 43% of sucrose converted.

24. The process of claim 20, wherein the *Streptococcus* glucosyltransferase enzyme is a *Streptococcus salivarius* glucosyltransferase enzyme or *Streptococcus sobrinus* glucosyltransferase enzyme.

* * * * *